(12) United States Patent
Teichmann

(10) Patent No.: US 6,761,713 B2
(45) Date of Patent: Jul. 13, 2004

(54) MEDICAL LASER UNIT

(75) Inventor: Heinrich-Otto Teichmann, Katlenburg-Lindau (DE)

(73) Assignee: Lisa Laser Products OHG Fuhrberg & Teichmann, Katlenburg-Lindau (DE)

( * ) Notice: Subject to any disclaimer, the term of this patent is extended or adjusted under 35 U.S.C. 154(b) by 104 days.

(21) Appl. No.: 10/010,482

(22) Filed: Nov. 8, 2001

(65) Prior Publication Data

US 2002/0049434 A1 Apr. 25, 2002

(30) Foreign Application Priority Data

Nov. 8, 2000 (DE) .......................................... 100 55 179

(51) Int. Cl.[7] .............................................. A61D 18/18
(52) U.S. Cl. ............................ 606/10; 606/11; 606/13; 606/15; 372/25; 372/29.02; 372/68; 372/70; 372/71
(58) Field of Search ................................. 606/7, 10–16; 372/25, 29.02, 68–71

(56) References Cited

U.S. PATENT DOCUMENTS 5,148,445 A * 9/1992 Liu et al. ...................... 372/70
5,234,006 A * 8/1993 Eaton et al. ................. 606/228
5,390,204 A * 2/1995 Yessik et al. .................. 606/11
5,549,600 A * 8/1996 Cho ............................. 606/15

OTHER PUBLICATIONS

D.G. Carlson, "Dynamics of a Repetitively Pump–Pulsed Nd:YAG Laser*", Aug. 1968, Journal of Applied Physics, vol. 39, No. 9.

G. Huber, "Festkörperlaser–neue Entwicklungen", Phys. B1.47 (1991) Nr. 5 No Translation.

* cited by examiner

Primary Examiner—David M. Shay
(74) Attorney, Agent, or Firm—Thomas, Kayden, Horstemeyer, Risley

(57) ABSTRACT

The medical laser unit (1) includes at least one laser body (3) being made of laser material (4). A first type of a pump light source (11) is designed and arranged to continuously excite the laser material (4) and to generate continuous laser radiation (7). A second type of a pump light source (16) is designed and arranged to excite the laser material (4) by pulses and to generate pulsed laser radiation (7). A transmitting unit is designed and arranged to transmit the continuous laser radiation (7) and the pulsed laser radiation (7) to a surgical application site. More particularly, the medical laser unit (1) has two modes of operation, a first mode for cutting with continuous laser radiation (7) and a second mode for fragmenting with pulsed laser radiation (7) of short time and high power laser pulses.

7 Claims, 1 Drawing Sheet

MEDICAL LASER UNIT

CROSS REFERENCE TO RELATED APPLICATIONS

This application claims the benefit of co-pending German Patent Application No. 100 55 179 entitled "Laservorrichtung, insbesondere für chirurgische Anwendungen", filed on Nov. 8, 2000.

FIELD OF THE INVENTION

The present invention generally relates to a laser unit. More particularly, the present invention relates to a medical laser unit to be used in the field of surgery. For medical applications and especially surgical applications, interaction between the laser radiation and the tissue is required. In surgical applications, it is desired to make it possible to cut soft tissue supplied with blood and also soft tissue not supplied with blood with the laser radiation only with a thin coagulation edge being located about the cutting region, but with sufficient hemostasis in any case. On the other hand, it is desired to be capable of coagulating soft tissue in a specific way and to fragment, erode or remove hard body materials by pulsed laser radiation of short time high power laser pulses. For example, the relevant hard materials may be bones, urinary concretion and gall stones. At the same time, it is desired to make the handling of the laser radiation as simple and safe as possible. It is ideal not to transmit the laser radiation as a free beam, but rather through a protected articulated mirror arm or an optical wave guide which delivers the laser radiation to the respective surgical site.

BACKGROUND OF THE INVENTION

Laser units which serve to produce either continuous laser radiation or pulsed laser radiation are known. A known laser for producing continuous laser radiation is produced and sold by the assignee of this application. It includes a laser rod made of laser material as a laser body. To excite the laser material, there is a plurality of laser diodes as pump light sources the pump light of which is introduced into the laser rod at its longitudinal end. The pump light is kept in the laser rod by index guidance, meaning total reflection, until it will be absorbed by the laser material over an absorption length of approximately the same size as twice the length of the laser rod. Cooling of the laser rod over its entire circumference with an enclosed cooling coat results in an rotational symmetric temperature distribution around the axis of the laser rod. Pump light which is not absorbed after the first pass through the laser material returns at the far end of the laser rod at an optical coating being highly reflective for the pump light wave length into the laser material for a second pass. The continuous laser radiation of the known laser unit has a wavelength in the region of 2 $\mu$m and it is suitable to cut and also just to coagulate soft tissue and to achieve excellent hemostasis in well circulated tissues like prostate, kidney and liver. Cutting power or cutting efficiency is good, and there are a good cutting results which have a thin coagulation edge which typically is less than approximately 1 mm. However, the continuous laser radiation of the known laser unit is not suitable to erode and to fragment hard materials.

Laser units for producing continuous laser radiation with laser diodes as pump light sources are also known in embodiments of known laser units including transversal pump geometries.

Furthermore, laser units in which a laser body made of laser material, for example also a laser rod, is excited by a flash lamp as pump light source in a transversal pump geometry are also known. The pump light power of a flash pump may be increased in a way that the pulse-like laser radiation is realized at pulse peak power in the multi Kilowatts region and the pulse energy of the single pulses occurs in the multi Joule region. However, the pulse repetition rate is limited by the decreasing laser efficiency with increasing laser material temperature which typically occurs under flash lamp pumping. A longitudinal pump geometry which would be interesting for thermal reasons is difficult to be realized with one flash lamp since the wavelength of the pump light for this purpose has to be adjusted to approach an energy level shortly above the transition to be excited to attain population inversion at the laser transition and the required absorption length in the laser rod. Such fine tuning is not possible with flash lamps which rather radiate in a wide-band way. Furthermore, geometric radiation characteristics of the flash lamp oppose to the introduction of the delivered pump light into the laser rod. The pulsed laser radiation of the known laser unit including the flash lamp as pump light source allows for eroding and fragmenting hard materials in a good way. The single pulses initiate shockwaves which destruct the respective hard material in a controlled manner. In case of pulsed laser radiation of the known pulsed laser, cutting power and cutting quality is not good in soft tissue. In case of high rates of pulses, cutting power and cutting quality is increased. However, the cut edges are strongly fringed due to the way of pulsing. Coagulation only of soft tissue is less efficient with pulsed laser radiation of which the repetition rate does not exceed 50 Hz in the known laser unit including a flash lamp as a pump light source compared to coagulation with continuous laser radiation of the other known continuous wave laser unit.

SUMMARY OF THE INVENTION

The present invention relates to a medical laser unit for surgical applications. The medical laser unit includes at least one laser body being made of laser material. A first type of a pump light source is designed and arranged to continuously excite the laser material and to generate continuous laser radiation. A second type of a pump light source is designed and arranged to excite the laser material by pulses and to generate pulsed laser radiation. A transmitting unit is designed and arranged to transmit the continuous laser radiation and the pulsed laser radiation to a surgical application site. More particularly, the present invention relates to a medical laser unit which has two modes of operation, a first mode for cutting and a second mode for fragmenting. The medical laser unit for surgical applications includes at least one laser rod being made of laser material, at least one laser diode being designed and arranged to continuously excite the laser material and to generate continuous laser radiation and at least one flash lamp being designed and arranged to excite the laser material by pulses and to generate pulsed laser radiation. The laser diode and the flash lamp are designed and arranged to excite the laser material of the laser rod to generate continuous laser radiation in a first mode of operation in which the laser diode excites the laser material above a laser threshold. In a second mode of operation, the laser diode and the flash lamp are designed and arranged to simultaneously excite the laser material of the laser rod to generate pulsed laser radiation, the laser diode exciting the laser material below the laser threshold and the flash lamp additionally exciting the laser material above the laser threshold. The unit further includes at least one transmitting unit being designed and arranged to transmit the continuous laser radiation and the pulsed laser radiation to a surgical application site.

The novel laser unit fulfills all requirements of surgical applications, meaning it is suitable to cut soft tissue with a thin coagulation edge and excellent hemostasis of well circulated tissue, to purely coagulate soft tissue as well as to erode and to fragment hard materials.

The novel laser unit leaves the known concept of fulfilling all requirements of surgical applications with one single way of generating laser radiation. Consequently, the novel medical laser unit includes both elements to produce or generate continuous laser radiation as well as such ones to produce pulsed laser radiation of high pulse peak power at a short pulse duration. The generation of continuous laser radiation is to be understood as either real so called continuous wave laser radiation or as quasi continuous wave laser radiation consisting of single pulses following one after the other very rapidly and overlapping. The repetition rate of the single pulses preferably is well above approximately 100 Hz. Preferably, it is at least approximately 200 Hz. Clean cutting of soft tissue without fringing effects of the cut edges is possible with such continuous laser radiation. If the suitable wavelength of the laser radiation determining its absorption in the tissue is chosen, thin layers of coagulated tissue are attained, and coagulation only of soft tissue is possible without problem. To fragment, disintegrate and ablate hard materials, the novel laser unit uses the known principle of pulsed laser radiation with the shockwave resulting therefrom. In this case, pulsed laser radiation means to include separate single pulses at high pulse peak power in the multi Kilowatts region and pulse energy of the single pulses in the multi Joule region. The high pulse peak power results in an immediate conversion of the absorbed laser energy, in the generation of heat and in the sudden evaporation of water being present in the respective tissue. The sudden increase of pressure inside hard materials, like bone or urinary concretion, results in fragmentation of this material. Only a comparatively small portion of the absorbed laser energy reaches the directly adjacent tissue due to thermal conduction, and it there leads to the desired coagulation which is spatially limited (not in uncirculated materials like, for example, kidney stones). Heat damage of the adjacent tissue is kept within the predetermined limits by a suitable choice of the average power and of the operating time of the laser.

For example, laser diodes belong to the first type of pump light sources for the generation of continuous laser radiation. For example, flash lamps belong to the other second type of pump light sources for originating pulsed laser radiation.

The laser material may be doped with $Tm^{3+}$ ions and/or with $Ho^{3+}$ ions. The ions $Tm^{3+}$ and $Ho^{3+}$ are the most known laser ions which have a laser wavelength of approximately 2 $\mu$m, meaning in the region of approximately 1.8 to 2.2 $\mu$m. This laser wavelength stands for an absorption length in soft tissue substantially consisting of water which leads to controlled coagulation and thin coagulation edges during cutting of soft tissue. In case a flash lamp is used as the second type of pump light source, the laser material may be further doped with $Cr^{3+}$ ions as a sentiziser for the white pump light of the flash lamp.

The pump light sources of the first type serving to generate continuous laser radiation may excite the laser material of a laser rod as laser body in a longitudinal and/or in a transversal pump geometry. The pump light sources of the other second type which serve to generate pulsed laser radiation may excite the laser material of a laser rod as laser body in a transversal pump geometry. These pump geometries correspond to separately known laser apparatuses.

In the novel laser unit, the laser material being excited by the pump light sources of the two types may be distributed to two laser bodies, at least the laser material of one laser body being excited by the pump light sources of the first type and the laser material of at least one other laser body being excited by the pump light sources of the second type. The two laser bodies may each be arranged in their own resonator. However, embodiments of the novel laser unit in which the pump light sources of the first type and of the other pump light sources of the second type excite the laser material of the same laser body are preferred. This means that the novel laser unit, for example, includes only one single laser rod made of laser material. This laser rod is then excited in longitudinal and/or in a transversal pump geometry by laser diodes. In the transversal pump geometry, excitation by a flash lamp serves to generate pulsed laser radiation.

In an especially preferred embodiment of the novel laser unit, the pump light sources of the second type excite the laser material of the laser rod while, at the same time, the laser material is excited by the pump light sources of the first type. The excitation of the laser material by the pump light sources of the first type remain below the laser threshold. In this example, this means that the laser material of the laser rod experiences basic excitation by the pump light coming from the laser diodes to generate pulsed laser radiation. The excitation of the laser material does not reach or exceed a laser threshold. To generate pulsed laser radiation, the laser threshold is shortly exceeded by additional pump light pulses produced by the flash lamp. The basic excitation or pre-excitation of the laser material may be utilized for the generation of pulsed laser radiation by the flash lamp excitation. Consequently, the entire laser pulse energy does not have to be achieved by the flash lamp which generally is less efficient and which generates more heat in the laser material than a narrow bandwidth laser diode with a suitable wavelength for minimized loss of quantum energy. In this way, it is possible to realize effective cooling of the laser rod over its radial circumference despite the high energy and the high power of the pulses released by the flash lamp. The flash lamp itself does not have to emit pump light of high energy and power because of the pre-excitation by the laser diodes. Thus, a comparatively affordable flash lamp providing white pump light even through a cooling coat for the laser rod is acceptable, whereas, normally, such a white pump light, if used at a power level to exceed the laser threshold alone, would heat up the laser material to an unacceptable extent. This is especially the case with $Ho^{3+}$ or $Tm^{3+}$ doped Laser materials and other laser ions with a strongly temperature depending gain. It is to be understood that—if both the continuous laser radiation and the pulsed laser radiation originates from the same laser material—the radiations have the same wave length. This is an advantage as the transmitting unit for both kinds of laser radiation only has to be adapted to one laser light wave length, and the laser light wavelength of both kinds of laser radiation may have the optimum wave length of approximately 2 $\mu$m. In the novel laser unit, it is possible to achieve continuous laser radiation of a laser power of approximately 100 Watts. For this purpose, the novel laser apparatus may also include a plurality of laser rods being arranged in series or in parallel. Not all of these laser rods have to be excitable by pump light sources of the second type in addition to their excitation by associated pump light sources of the first type. The double excitation of one single laser rod by pump light sources of both types generally is sufficient to generate continuous and pulsed laser radiation.

In the novel laser unit, the pulsed laser radiation may reach a pulse peak power of approximately 10 kW at pulses of approximately 0.5 to 1.0 msec pulse duration and approximately 1 Joule pulse energy. In this way, effective erosion and fragmentation of hard materials is realized at minimum thermal effects.

Other features and advantages of the present invention will become apparent to one with skill in the art upon examination of the following drawings and the detailed description. It is intended that all such additional features and advantages be included herein within the scope of the present invention, as defined by the claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. In the drawings, like reference numerals designate corresponding parts throughout the several views.

DETAILED DESCRIPTION

Figure 1:
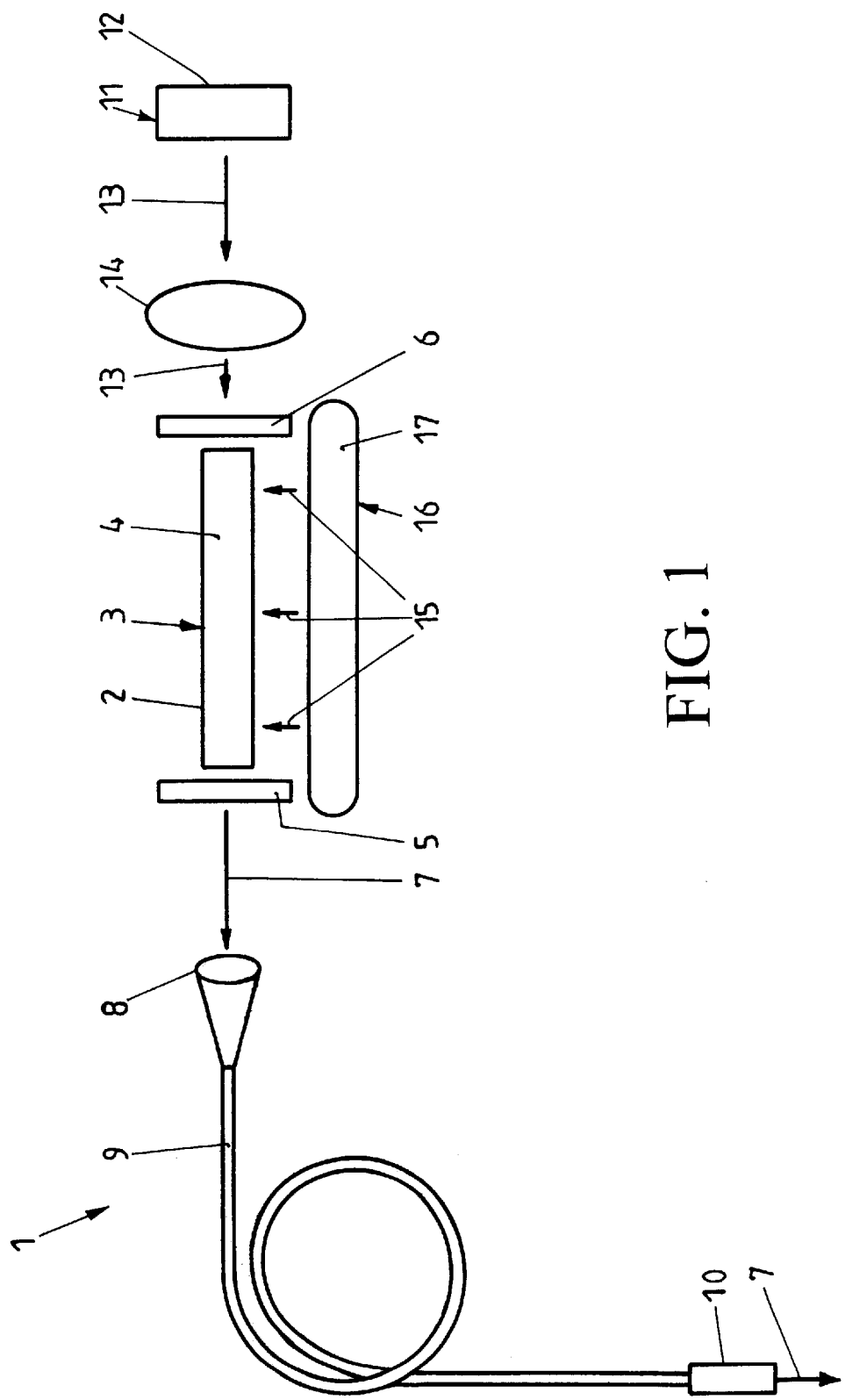
FIG. 1 is a view of the general construction of the novel laser unit.

Referring now in greater detail to the drawing, FIG. 1 illustrates a view of the novel laser unit 1 including a laser rod 2 as laser body 3, the laser rod 2 being made of laser material 4. The laser rod 2 is arranged between two resonator mirrors 5 and 6. Laser radiation 7 exits from the resonator formed by elements 5, 2, 6 via the resonator mirror 5, and it is introduced into an optical wave guide 9 by an optical element 8. For example, the optical wave guide 9 may be based on an optical quartz fiber. Via the optical wave guide 9, the laser radiation reaches a hand piece or an applicator 10 where it is used in a surgical site. A pump light source 11 is arranged to excite the laser material 4, the pump light source 11 being a laser diode stack 12. The pump light 13 coming from the pump light source 11 is introduced into the laser rod 2 in a longitudinal direction via an optical element 14 and the resonator mirror 6 which is permeable to the pump light 13. The laser rod 2 is excited by the pump light source 11 to produce continuous laser radiation 7. The laser material 4 is excited by the pump light 13 above the laser threshold of the laser material 4. To produce pulsed laser radiation 7 with the same unit 1, the laser material 4 is excited by the pump light 13 shortly below its laser threshold. To initiate the separate laser pulses, there is an additional excitation with pump light 15 by a pump light source 16 being designed as a flash lamp 17. The pump light 15 excites the laser material 4 above the laser threshold, and in this way, it initiates the single pulses of laser radiation 7. With this method, there is the advantage of a temperature profile of a radial symmetry building up in the laser rod 2 due to the continuous excitation of the laser body 33 with laser light 13, the pump light being absorbed while it passes through the laser material 4 of the laser rod 2 which is cooled from the outside. The radial temperature profile pre-stabilizes the resonator 5, 2, 6 in a way as if the resonator 5, 2, 6 was already used during repeated operation in a usual generation of pulsed or continuous laser radiation 7. As a result, pulse to pulse stability in the starting phase of the laser unit 1 is improved. Due to the pre-excitation with the pump light 13 just below the laser threshold of the laser material 4 by the pump light 13, it is only necessary to introduce less excitation energy into the laser rod 2 by the flash lamp 14 to initiate a single pulse of the laser radiation 7 compared to all laser ions in the laser rod being in their energetic ground state before excitation by the flash lamp 17. Correspondingly, the electrical expenditure for the flash lamp 17 is reduced. Furthermore, spectral narrow-band pumping may be conducted with the pump light 13 of the laser diode stack 12. Consequently, less power loss occurs in the laser rod 2 compared to spectral wide-band pumping by the flash lamp 17. For the production of pulsed laser radiation 7, the heat load acting upon the laser material is substantially reduced compared to the generated heat load under flash lamp excitation only. This is especially significant in laser material 4 being doped with trivalent Tm ions and Ho ions, respectively, in which the lower laser level only is a few 100 cm$^{-1}$, above the absolute ground state, and the upper laser level is at the lower end of a multiplet of energetic states with a spreading in the order of 100 cm$^{-1}$. In case of an increase of temperature occurring inside the laser body 3 which may result from dissipated heat out of the pump light 15, the lower laser level is thermally populated, the upper laser level is depopulated and the laser threshold is increased. As a result, efficiency of the laser unit 1 is strongly reduced. In the novel laser unit 1, this adverse effect is significantly reduced by the flash lamp 17 with comparatively less efficiency of the pump light 15 only being used to exceed the laser threshold of the laser material 4.

The FIGURE shows an arrangement in which the pump light 13 excites the laser rod 2 in a longitudinal pump geometry, whereas the pump light 15 excites the laser rod 2 in a transversal pump geometry. Generally, it is possible to change the two pump geometries in a way that the continuous laser radiation is produced with the transversal pump geometry and the pulsed laser radiation is initiated with the longitudinal pump geometry. Additionally, the pump light 13, as well as the pump light 15, may excite the laser rod 2 in the transversal pump geometry and in the longitudinal pump geometry, respectively. The arrangement of the novel laser unit 1 as illustrated in FIG. 1 is the presently preferred exemplary embodiment of the novel laser unit 1.

Many variations and modifications may be made to the preferred embodiments of the invention without departing substantially from the spirit and principles of the invention. All such modifications and variations are intended to be included herein within the scope of the present invention, as defined by the following claims.

I claim:

1. A medical laser unit for surgical applications, comprising:

at least one laser rod being made of laser material;

at least one laser diode being designed and arranged to continuously excite the laser material and to generate continuous laser radiation;

at least one flash lamp being designed and arranged to excite the laser material by pulses and to generate pulsed laser radiation, said laser diode being designed and arranged to excite the laser material of said laser rod to generate continuous laser radiation in a first mode of operation in which said laser diode excites the laser material above a laser threshold, and said laser diode and said flash lamp being designed and arranged to simultaneously excite the laser material of said laser rod to generate pulsed laser radiation in a second mode of operation in which said laser diode excites the laser material below the laser threshold and said flash lamp additionally excites the laser material above the laser threshold; and at least one transmitting unit being designed and arranged to transmit the continuous laser radiation and the pulsed laser radiation to a surgical application site.

2. The medical laser unit of claim 1, wherein the laser material is doped with $Tm^{3+}$ ions.

3. The medical laser unit of claim 1, wherein the laser material is doped with $Ho^{3+}$ ions.

4. The medical laser unit of claim 1, wherein the laser material is doped with $Tm^{3+}$ and $Ho^{3+}$ ions.

5. The medical laser unit of claim 1, wherein said laser diode is designed and arranged to excite the laser material of said laser rod in a longitudinal pump geometry, and said flash lamp is designed and arranged to excite the laser material of said laser rod in a transversal pump geometry.

6. The medical laser unit of claim 1, wherein the continuous laser radiation reaches a laser power of approximately 100 W.

7. The medical laser unit of claim 1, wherein the pulsed laser radiation reaches a pulse peak power of approximately 10 kW at a pulse duration of approximately 0.5 to 1.0 msec.

* * * * *